US010278866B2

(12) United States Patent
Moore et al.

(10) Patent No.: US 10,278,866 B2
(45) Date of Patent: May 7, 2019

(54) GOGGLES WITH DETACHABLE FACEMASK

(71) Applicant: The Burton Corporation, Burlington, VT (US)

(72) Inventors: Trevor J. Moore, Richmond, VT (US); James D. Laughlin, Burlington, VT (US)

(73) Assignee: The Burton Corporation, Burlington, VT (US)

( * ) Notice: Subject to any disclaimer, the term of this patent is extended or adjusted under 35 U.S.C. 154(b) by 246 days.

(21) Appl. No.: 14/086,440

(22) Filed: Nov. 21, 2013

(65) Prior Publication Data

US 2015/0135419 A1 May 21, 2015

(51) Int. Cl.
*A61F 9/02* (2006.01)

(52) U.S. Cl.
CPC .............. *A61F 9/028* (2013.01); *A61F 9/029* (2013.01)

(58) Field of Classification Search
CPC ............ A41D 13/1161; A41D 13/1184; A41D 13/11; A41D 13/1146; A41D 13/1218; G02C 11/00; A61F 9/029; A61F 9/028; A61F 9/025; A61F 9/04; A61F 9/06; A61F 9/045
USPC ........ 2/436, 206, 13, 12, 426–429, 437, 438
See application file for complete search history.

(56) References Cited

U.S. PATENT DOCUMENTS

| 1,035,217 A * | 8/1912 | McQuary, Jr. .......... A61F 9/029 128/206.24 |
| 1,582,164 A * | 4/1926 | Burstyn ............. A41D 13/1184 128/863 |
| 1,635,328 A * | 7/1927 | Kintz ...................... A61F 9/025 2/10 |
| 1,947,137 A * | 2/1934 | Fraser ..................... A61F 9/028 2/436 |
| 2,026,741 A * | 1/1936 | Kintz ...................... A61F 9/025 2/10 |
| 2,435,653 A * | 2/1948 | Maurer ................... A61F 9/028 128/201.15 |
| 2,665,686 A * | 1/1954 | Wood .................... A41D 13/11 128/206.12 |

(Continued)

FOREIGN PATENT DOCUMENTS

| FR | 3016271 A1 * | 7/2015 | ......... A41D 13/1153 |
| WO | WO 2006/125167 A2 | 11/2006 | |

OTHER PUBLICATIONS

Dimitri Poliderakis, "North45—Reinventing the Scarf," Kickstarter.com, Nov. 27, 2013.

(Continued)

*Primary Examiner* — Anna K Kinsaul
*Assistant Examiner* — F Griffin Hall
(74) *Attorney, Agent, or Firm* — Wolf, Greenfield & Sacks, P.C.

(57) ABSTRACT

A support frame for releasably attaching a facemask to a goggle including at least one vent and its method of use are described. In one non-limiting embodiment, the support frame includes a nose bridge and two legs extending from the nose bridge. The nose bridge and the two legs are adapted and arranged to releasably attach the facemask to a bottom surface of the goggles. The nose bridge and two legs are arranged such that the at least one vent is unobstructed when the facemask is attached to the goggles by the support frame.

29 Claims, 8 Drawing Sheets

(56) References Cited

U.S. PATENT DOCUMENTS

| | | | | |
|---|---|---|---|---|
| 2,669,717 | A | * | 2/1954 | Diggs ............... A41D 13/1184 2/12 |
| 3,298,031 | A | * | 1/1967 | Morgan ............ A41D 13/1184 2/427 |
| 3,945,044 | A | * | 3/1976 | McGee ................. A61F 9/025 2/436 |
| 4,250,577 | A | | 2/1981 | Smith |
| 4,300,240 | A | * | 11/1981 | Edwards ........... A41D 13/1161 2/206 |
| 4,653,124 | A | * | 3/1987 | McNeal ................. A61F 9/029 128/206.21 |
| 4,821,340 | A | * | 4/1989 | Johnson ................ A41D 13/11 128/863 |
| 4,944,039 | A | | 7/1990 | Dietrich |
| 5,107,543 | A | * | 4/1992 | Hansen ............. A41D 13/1146 2/426 |
| D367,664 | S | * | 3/1996 | Simioni ..................... D16/309 |
| D370,230 | S | * | 5/1996 | Simioni ..................... D16/309 |
| 5,697,100 | A | * | 12/1997 | Horowitz .......... A41D 13/1161 2/13 |
| 5,704,063 | A | * | 1/1998 | Tilden ............... A41D 13/1107 128/857 |
| 6,009,555 | A | * | 1/2000 | Siprut ................... A42B 1/247 2/12 |
| 6,065,833 | A | * | 5/2000 | Tiano ..................... A61F 9/029 2/435 |
| 6,272,690 | B1 | * | 8/2001 | Carey .................... A41D 13/11 2/171 |
| 7,475,982 | B2 | * | 1/2009 | Welchel ............ A41D 13/1184 351/158 |
| 7,488,068 | B2 | | 2/2009 | Welchel et al. |
| D594,895 | S | * | 6/2009 | Ross ........................... D16/309 |
| D599,394 | S | * | 9/2009 | Dondero .................... D16/312 |
| 8,185,969 | B2 | | 5/2012 | Chang |
| 8,225,431 | B2 | * | 7/2012 | Cyr ......................... A42B 3/22 2/15 |
| 8,549,662 | B2 | | 10/2013 | Chang |
| 8,857,433 | B1 | * | 10/2014 | Kelly ..................... A61B 90/05 128/206.24 |
| 9,693,596 | B2 | * | 7/2017 | Huffman ................ A42B 3/20 |
| 2006/0085883 | A1 | * | 4/2006 | Tan .................... A41D 13/1107 2/9 |
| 2007/0033716 | A1 | * | 2/2007 | Dondero ................ A61F 9/025 2/426 |
| 2007/0050896 | A1 | * | 3/2007 | Stevens ................... A42B 3/20 2/427 |
| 2007/0252946 | A1 | * | 11/2007 | Welchel ............ A41D 13/1184 351/62 |
| 2007/0261155 | A1 | * | 11/2007 | Tabacchi ................ A61F 9/025 2/439 |
| 2008/0127400 | A1 | * | 6/2008 | Dupuis .................. A42B 3/105 2/424 |
| 2010/0005575 | A1 | * | 1/2010 | Dondero ................ A61F 9/025 2/428 |
| 2010/0186153 | A1 | * | 7/2010 | Reyes .................... A61F 9/029 2/427 |
| 2013/0014316 | A1 | * | 1/2013 | Castro ............... A41D 13/1184 2/424 |
| 2013/0185849 | A1 | * | 7/2013 | Laughlin ............... A61F 9/025 2/431 |
| 2014/0196200 | A1 | * | 7/2014 | Beliveau ................ A41D 13/11 2/424 |
| 2014/0259253 | A1 | * | 9/2014 | Jacob ................ A41D 13/1161 2/15 |
| 2015/0245675 | A1 | * | 9/2015 | Chinquee ........... A41D 13/1184 2/424 |
| 2015/0351468 | A9 | * | 12/2015 | Chinquee ........... A41D 13/1184 2/424 |

OTHER PUBLICATIONS

International Preliminary Report on Patentability for Application No. PCT/US2014/066847, dated May 24, 2016.

International Search Report and Written Opinion for Application No. PCT/US2014/066847, dated Apr. 8, 2015.

* cited by examiner

GOGGLES WITH DETACHABLE FACEMASK

FIELD

Disclosed embodiments are related to goggles including a detachable facemask.

BACKGROUND

Goggles are used in any number of activities ranging from sports such as skiing and snowboarding to protective eyewear for use in a lab or even military situations. In instances where these goggles may be prone to fogging, the goggles may include various features such as vents, antifogging coatings, sealed double lenses, and other appropriate features. In some instances, an individual may also use various types of face protection in combination with the goggles. For example, a ballistic facemask intended to protect an individual during a combat situation might be used, or a thermal facemask might be used to keep an individual warm while outside. While specific types of facemasks are noted above, other types of facemasks can also be used.

SUMMARY

In one embodiment, a support frame for releasably attaching a facemask to a corresponding set of goggles, that may include at least one vent, includes a nose bridge and two legs extending from the nose bridge. The nose bridge and the two legs may be adapted and arranged to releasably attach the facemask to a bottom surface of the goggles. The nose bridge and the two legs may also be arranged such that the at least one vent is substantially unobstructed when the facemask is attached to the goggles by the support frame.

In another embodiment, a method of attaching a facemask to a pair of goggles may include attaching a support frame associated with the facemask to a bottom surface of the goggles, wherein the bottom surface of the goggles includes at least one vent, and wherein the at least one vent is unobstructed when the facemask is attached to the goggles by the support frame.

In yet another embodiment, a support frame for releasably attaching a facemask to a goggle including at least one vent may include a nose bridge and two legs extending from the nose bridge. The nose bridge and the two legs may be adapted and arranged to releasably attach the facemask to a bottom surface of the goggles. The nose bridge and the two legs may also be arranged to position the facemask relative the bottom surface of the goggles to prevent exhaled air of a person wearing the goggles from directly entering the at least one vent when the facemask is attached to the goggles by the support frame.

In another embodiment, a goggle system for releasably attaching a facemask may include a goggle including a top surface, a bottom surface, and two opposing side surfaces. The bottom surface may include at least one vent and one or more support surfaces that do not obstruct the at least one vent. The goggle system may also include a support frame including a nose bridge and two legs extending from the nose bridge. The nose bridge and the two legs may include one or more attachment points to releasably attach the support frame to the bottom surface. The nose bridge and the two legs may also follow a contour of the bottom surface and be disposed on the one or more support surfaces.

In yet another embodiment, a facemask system releasably attachable to a goggle may include a support frame including a nose bridge and two legs extending from the nose bridge. The nose bridge and the two legs may include one or more attachment points to releasably attach the support frame to a bottom surface of the goggle including at least one vent. The nose bridge and the two legs may also follow a contour of the bottom surface and be disposed on one or more support surfaces of the bottom surface such that the at least one vent is substantially unobstructed when the support frame is attached to the goggles. The facemask system may also include a facemask including an upper edge, where at least a portion of the upper edge is attached to the support frame.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings.

DETAILED DESCRIPTION

The inventors have recognized several issues associated with the use of facemasks that do not directly attach to a corresponding pair of goggles. For instance, the inventors have recognized that users may oftentimes position their facemask on top of an exterior surface of their goggles which may result in the person breathing directly into one or more vents located on a bottom surface of the goggles. Exhaling into these vents may result in increased temperature and humidity within the goggle interior which may lead to condensation forming on the goggle lenses. The inventors have also recognized that some individuals may position a facemask between a pair of goggles and their skin. Positioning a facemask in this fashion may create gaps between a person's face and the facemask, or between the facemask and the goggles. These gaps may result in the introduction of external air into the goggle interior. In instances where an individual is located in a cold environment, cold external air introduced into the goggle interior may result in condensation forming on the goggle lenses.

In addition to the use of facemasks that are not attached to a corresponding pair of goggles, some facemasks may be attached to the goggles. However, the inventors have recognized that when attached, these facemasks are arranged such that they obscure the vents located on the bottom surface of the goggles. This may result in reduced airflow into the goggle interior resulting in increased humidity and temperatures within the goggle interior which may lead to condensation forming on the goggle lenses. These facemasks also leave gaps between a bottom surface of the goggles and the facemask. When a person wearing such a goggle and facemask combination exhales, their breath may pass through these gaps. Since these gaps may be located adjacent to the one or more vents on the bottom surface of the goggles, the person's breath may directly enter the vents which may result in increased humidity and temperatures within the goggle interior which may again lead to condensation forming on the goggle lenses.

In view of the above, the inventors have recognized the benefits associated with attaching a facemask to a bottom surface of a pair of goggles such that it substantially prevents exhaled air from a person wearing the goggles from directly entering vents located along the one or more edges of the goggles. The inventors have also recognized the benefits associated with leaving the vents located along the edges of the goggles substantially unobstructed when the facemask is attached thereto. By substantially preventing exhaled air from entering the goggles, and/or by maintaining the vents located along the edges of the goggles substantially unobstructed, appropriate ventilation of the goggles may be maintained. This in turn may help to maintain a desired temperature and humidity characteristic of the goggle interior when worn to help prevent the formation of condensation on the goggle lenses.

In one possible embodiment, a facemask may be selectively attached to a pair of goggles using a support frame that the facemask is associated with. The support frame may include a nose bridge and two legs extending from the nose bridge. The nose bridge and the two legs may be adapted and arranged to attach the facemask to a bottom surface of the goggles which includes at least one vent. The nose bridge and the two legs may be arranged such that the at least one vent is substantially unobstructed when the facemask is attached to the goggles by the support frame. Depending on the embodiment, the support frame may be attached along an entire length of the bottom surface of the goggles, though embodiments in which the support frame attaches to only a portion of the bottom surface of the goggles are also possible.

When attached to a pair of goggles, a support frame may follow a contour of the goggles and/or be held flush against the goggles. Depending on the embodiment, the support frame may be held flush against the goggles along substantially an entire length of the support frame or only a portion of the length of the support frame as the disclosure is not so limited. Without wishing to be bound by theory, following a contour of the goggles and/or holding the support frame flush against the goggles may help to avoid gaps between the support frame and the goggles where a person's breath from inside the facemask might be directed toward at least one vent on a bottom surface of the goggles. In some embodiments, the support frame may include multiple attachment points for attaching the support frame to the goggles to help ensure that the support frame remains flush relative to a surface of the goggles along substantially its entire length. For example, the support frame might include at least one attachment point on each of a nose bridge and two legs extending therefrom. However, it should be understood that any number of attachment points, including a single attachment point, might also be used to attach the support frame to the goggles.

The support frame may be used to attach an associated facemask to a pair of goggles in any number of different ways as the disclosure is not so limited. For example, the support frame may be attached directly to the goggles, and the facemask may be attached to a lower portion of the support frame. Alternatively, at least a portion of the facemask may be positioned between the support frame and the goggles when the support frame is attached thereto. One example of such an embodiment is when an upper edge of a facemask is folded over an associated support frame and sewn together to form a hem that the support frame is positioned within. In some embodiments, this hem may include a slit through which the support frame may be inserted and/or withdrawn.

The support frame may be selectively attached to the goggles using any appropriate method. For example, the support frame may be attached to the goggles using a magnetic attachment, a mechanical interference fit, interlocking features, and/or a hook and loop fastener. Combinations of these attachment features may also be used. Magnetic attachments may be of particular benefit when it is desired to cover the support frame with the facemask such that an attachment through the facemask material is provided. Magnetic attachments may also offer the benefit of self alignment and increased durability as compared to other attachment methods.

For the purposes of this application, the terms flush, adjacent, attached, supported, and other similar terms refer both to instances where components are directly associated with one another and instances where components are indirectly associated with one another. For example, as noted above the support frame may be attached to, and held flush against, a bottom surface of the goggles. While the support frame and goggles might be in direct contact, in some embodiments, at least a portion of the facemask may be located between the support frame and the bottom surface of the goggles. Therefore, these terms are meant to encompass both possibilities. So, unless something is referred to as being directly flush, directly adjacent, directly attached, and/or directly supported by another component, the disclosure should be interpreted broadly as covering both direct and indirect relations of the noted components.

Turning now to the figures, several specific non-limiting embodiments are described in more detail.

Figure 1:
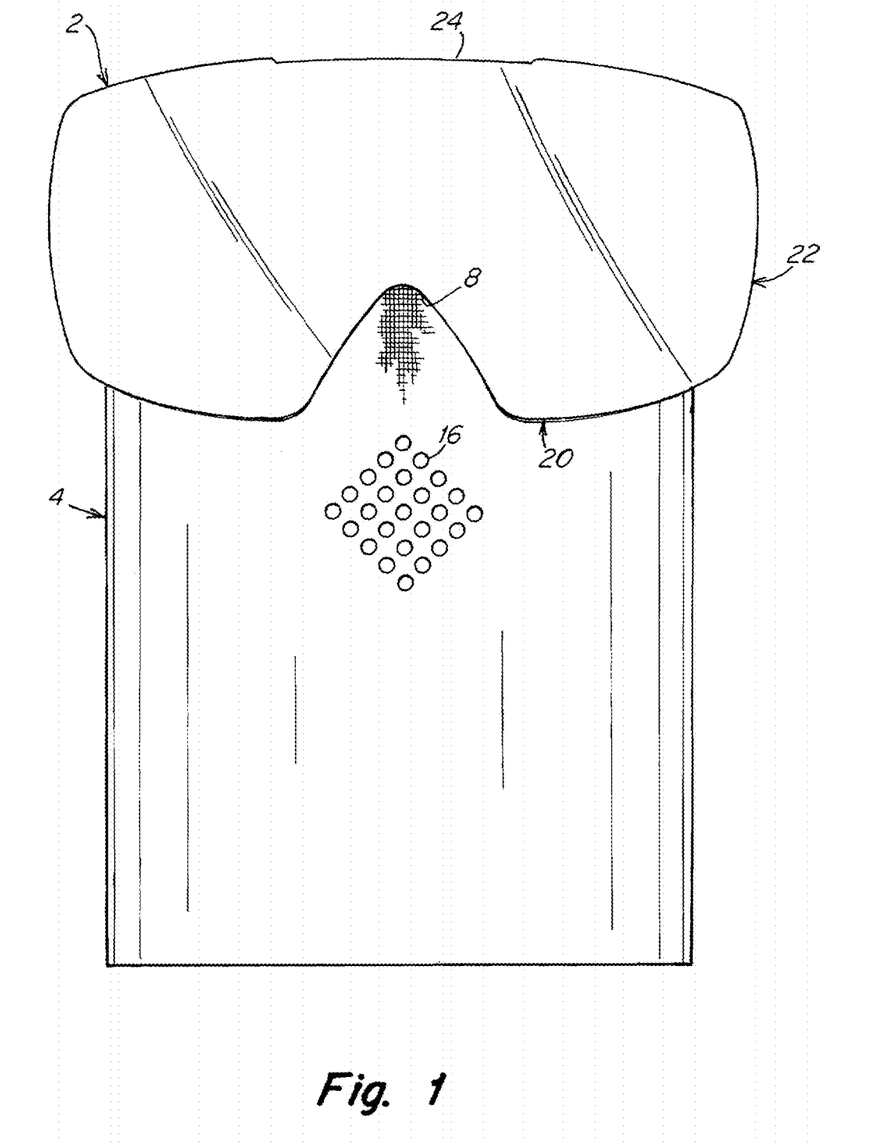
FIG. 1 is a schematic front view of a pair of goggles and an attached facemask.
Figure 2:
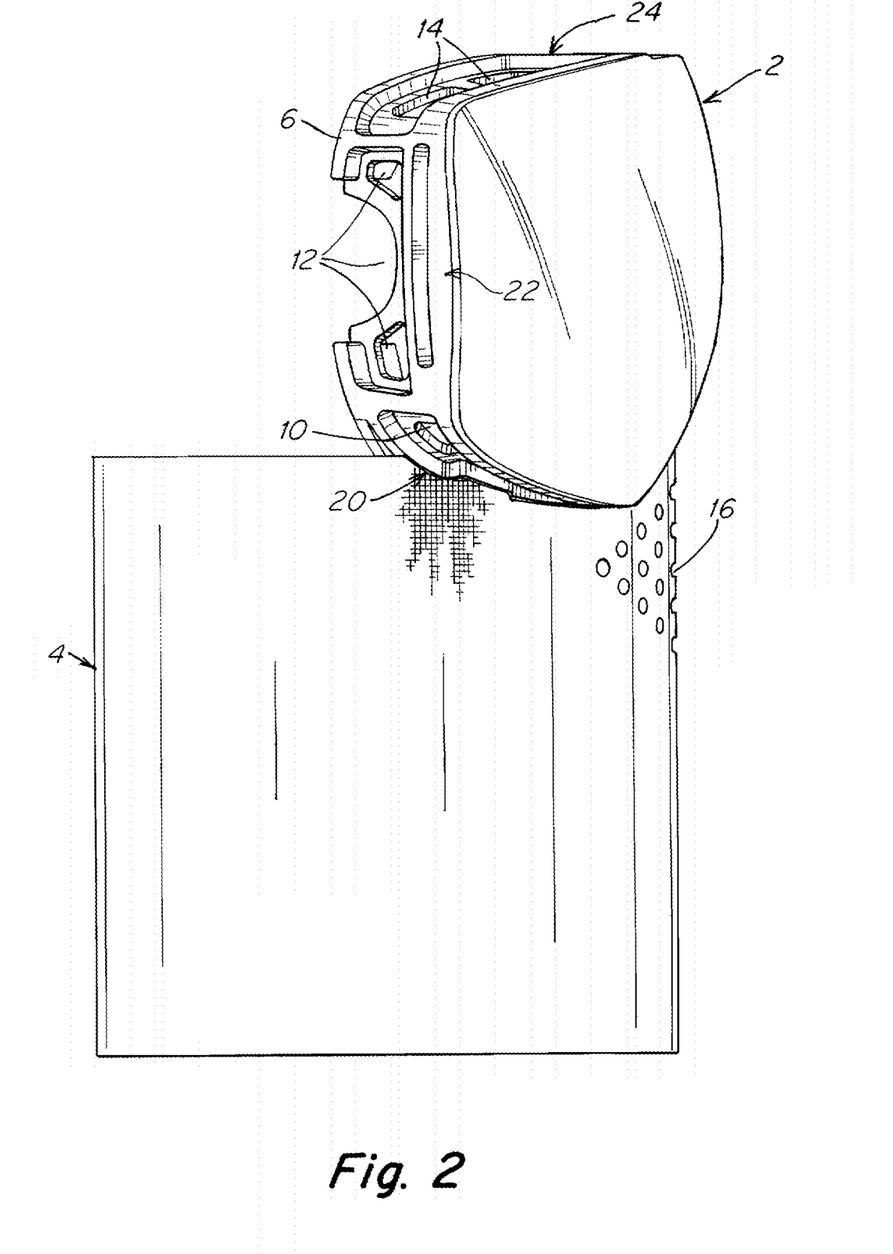
FIG. 2 is a schematic side view of the pair of goggles and the attached facemask of FIG. 1.
Figure 3:
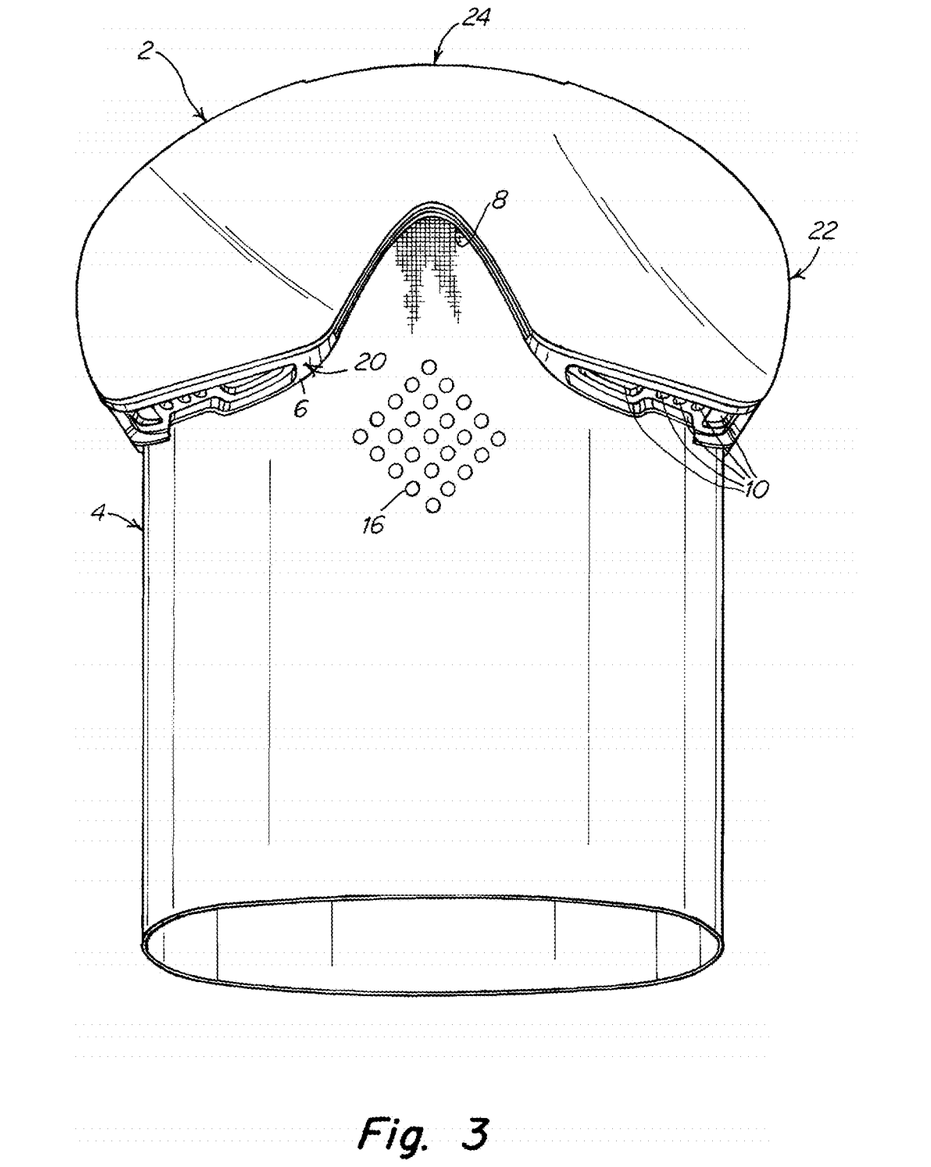
FIG. 3 is a schematic perspective bottom view of the pair of goggles and the attached facemask of FIG. 1.

FIGS. 1-3 present various views of one embodiment of a pair of goggles 2 and an attached facemask 4 which may include a breathing vent 16 or other appropriate breathing arrangement. As depicted in the figures, the goggles 2 may include a goggle frame 6 which includes a nose bridge 8. The goggle frame 6 may also include a plurality of vents such as a plurality of bottom vents 10 located along a bottom surface 20 of the goggles, a plurality of side vents 12 located on a side surface 22 of the goggles, and a plurality of top vents 14 located along a top surface 24 of the goggles. Other vent arrangements are also possible. The facemask may be attached to the goggles such that it does not substantially obscure the bottom vents 10 of the goggles 2. However, in some embodiments, the facemask 4 might obscure a small portion of the vents it is associated with such that the vents remain substantially unobscured and permit sufficient ventilation of the goggle interior to prevent condensation on an interior surface of the goggle lenses. Depending on the particular embodiment, the facemask 4 may be attached to substantially all of the bottom surface 20 of the goggles. However, embodiments in which the facemask is only attached to a portion of the bottom surface 20 of the goggles are also possible. Additionally, while it has not been depicted in the figures, the facemask may also be attached to the side and/or top of the goggles such that the side vents 12 and top vents 14 remain substantially unobstructed as well.

For the sake of clarity in depicting the relative positioning of the facemask and the vents, the vents have been depicted as being uncovered. However, these vents are typically covered using porous foam or another appropriate covering. As depicted in the figures, the vents may be embodied by a number of different shapes such as circular holes, elongated slots, semicircular cutouts, and other appropriate shapes. In view of the above, the vents should not be construed as being limited to any particular construction or arrangement as the disclosure is not so limited.

Figure 4:
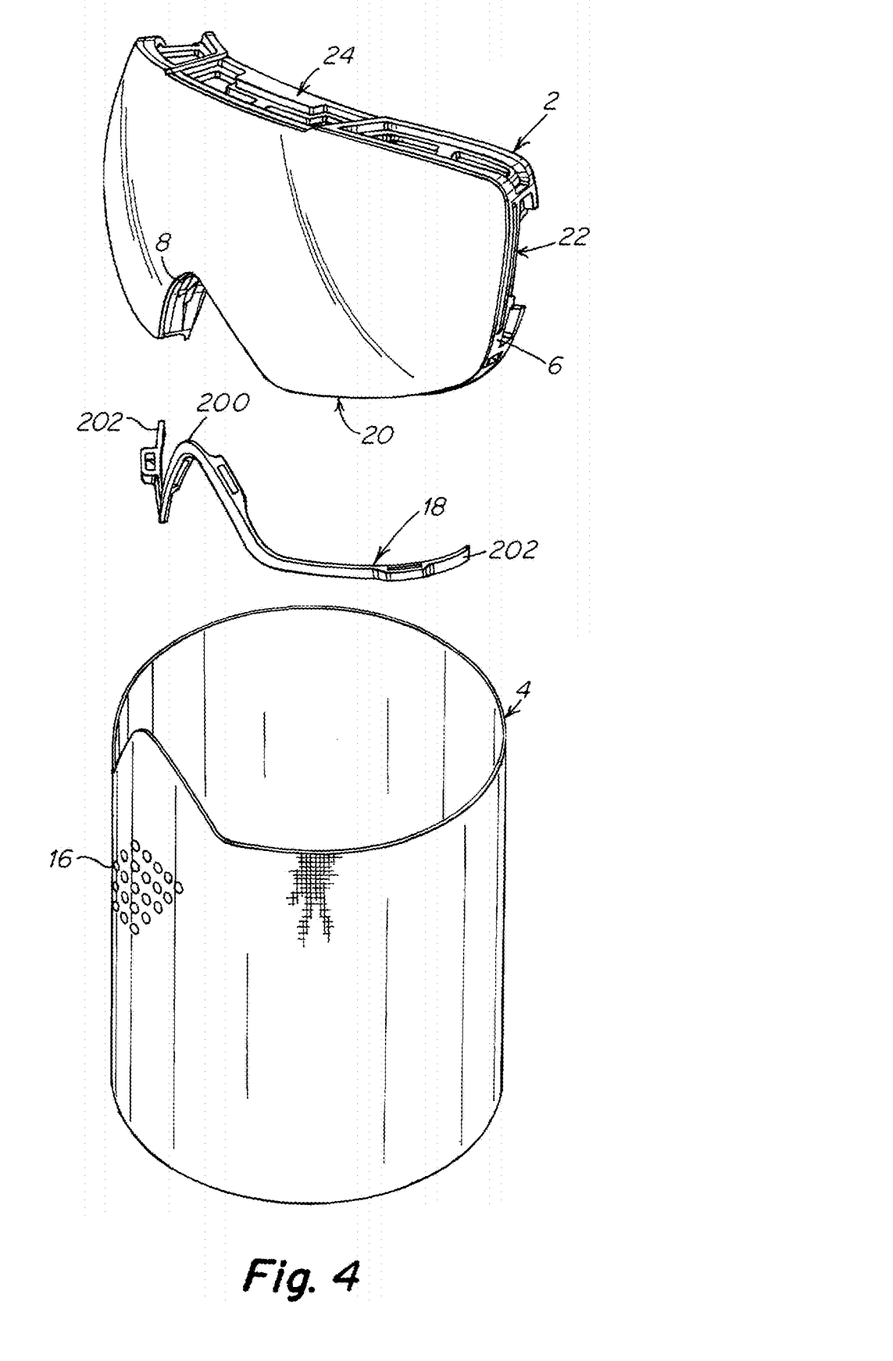
FIG. 4 is a schematic exploded perspective view of the pair of goggles and the attached facemask of FIG. 1.

FIG. 4 depicts an exploded perspective view of a facemask and goggle combination. As depicted in the figure, the facemask 4 may include a support frame 18 that is sewn into an upper edge of the facemask 4. The support frame 18 may include a triangular shaped nose bridge 200 and two legs 202 extending away from opposing ends of the nose bridge. However, other shapes and arrangements of both the nose bridge and legs are also possible. As described in more detail below, the nose bridge 200 and the two legs 202 of the support frame 18 may be shaped and arranged to attach the facemask 4 to the goggles 2 while leaving the vents located on the goggles substantially unobstructed.

For illustrative purposes, the goggles and support frames depicted in FIGS. 5-13 show cavities on one side of the component and magnets disposed in the cavities on the other side of the component. However, it should be understood that when fully assembled, magnets may be disposed in the depicted cavities of the goggles and the support frame. Additionally, other types of attachments might also be used.

Figure 5:
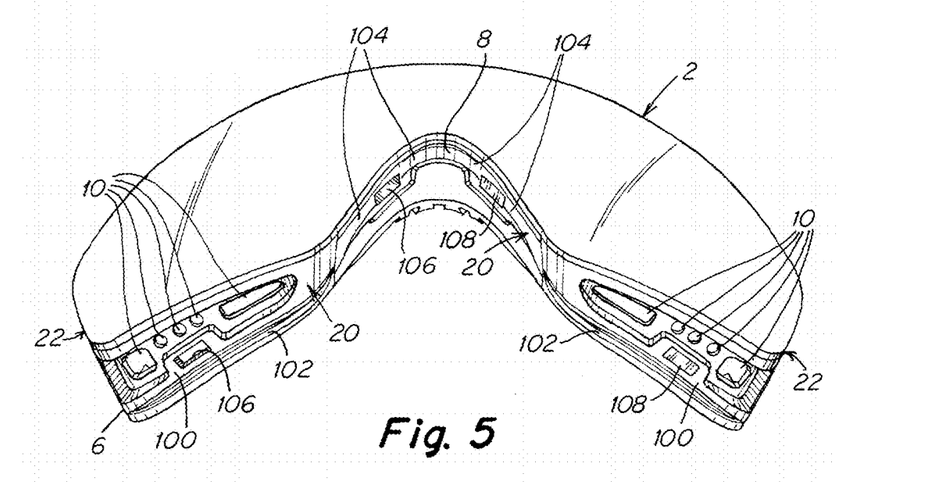
FIG. 5 is a schematic perspective bottom view of a pair of goggles.
Figure 6:
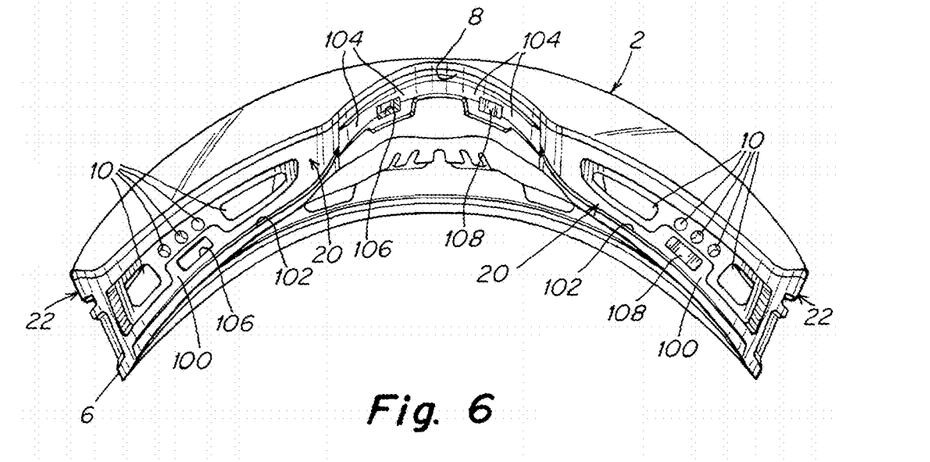
FIG. 6 is a schematic bottom view of the pair of goggles of FIG. 5.
Figure 7:
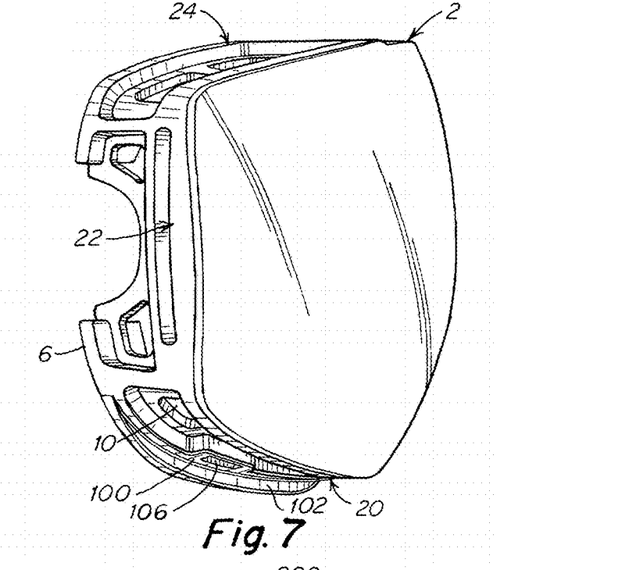
FIG. 7 is a schematic side view of the pair of goggles of FIG. 5.
Figure 8:
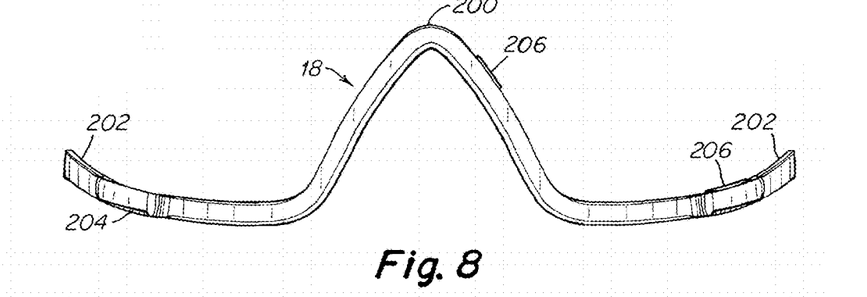
FIG. 8 is a schematic front view of a support frame.
Figure 9:
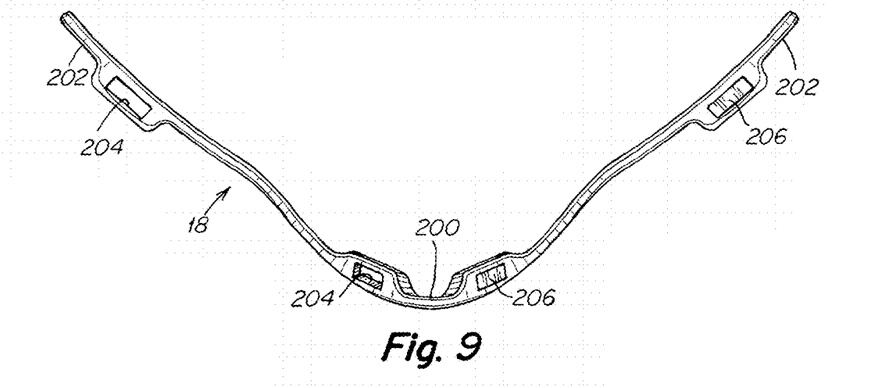
FIG. 9 is a schematic top view of the support frame of FIG. 8.
Figure 10:
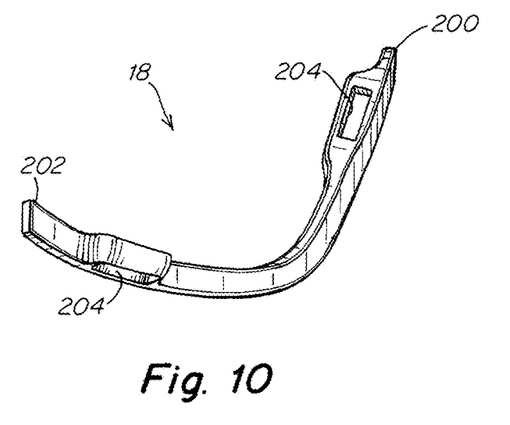
FIG. 10 is a schematic side view of the support frame of FIG. 8.
Figure 11:
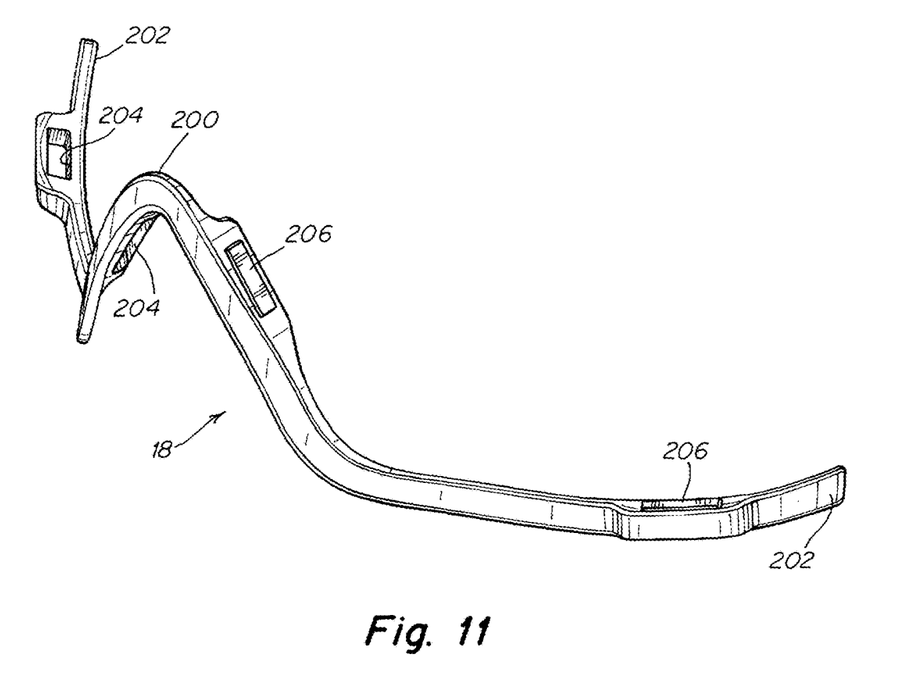
FIG. 11 is a schematic perspective view of the support frame of FIG. 8.

Various features of the goggles are illustrated in more detail in FIGS. 5-7. In the depicted embodiment, in addition to the bottom vents 10 and nose bridge 8, the goggles may also include support surfaces 100 and 104 as well as a shelves 102 located on a bottom surface 20 of the goggles to help support and position the support frame. The shelves 102 are located on both the right and left side of the goggle bottom surface 20 corresponding to the individual legs of support frame, not pictured. The goggles 2 may also include cavities 106 and magnets 108 disposed in the cavities for attaching the support frame thereto. While these features have been depicted on the bottom surface of the goggles, embodiments in which these features are also present on the side and/or top surfaces of the goggles are also possible.

As noted above, the support surfaces 100 and 104 may be used to help support and position the support frame while avoiding obstruction of the bottom vents 10 by either the support frame or the support surfaces when the support frame is attached to the goggles. In the depicted embodiment, the support surfaces 100 are located on a bottom surface 20 of the goggles 2 and are located on either side of the nose bridge 8. These surfaces are shaped and arranged to support the corresponding legs of the support frame. The two support surfaces 100 also transition to the support surface 104 located within the nose bridge 8 on the bottom surface 20 of the goggles as well. While the support surface 104 may correspond to any appropriate shape, in some embodiments, and as depicted in the figure, support surface 104 may correspond to a recessed groove. In some embodiments, the support surfaces 100 may also be embodied by grooves or recesses. Without wishing to be bound by theory, using a recessed groove may help in positioning and aligning a corresponding portion of the support frame during attachment.

Similar to the support surfaces 100 and 104, one or more shelves 102 can also be used to help position and support a support frame during attachment and use. In one embodiment, a shelf may include a front facing surface positioned on a bottom surface 20 of the goggles. In the embodiment depicted in the figures, two shelves 102 are depicted on either side of the nose bridge 8 and extend from the nose bridge 8 outwards towards a side surface 22 of the goggles. The one or more shelves 102 may be shaped and arranged such that it engages with at least a portion of a rearward facing surface of a corresponding support frame. Without wishing to be bound by theory, this may help to position the support frame on the goggles during attachment and may also help to prevent the support frame from being inadvertently displaced off of a rear edge of the goggles during use.

Depending on the embodiment, the support surfaces 100 and 104 as well as the one or more shelves 102 may be smooth and/or continuous. Without wishing to be bound by theory, this may facilitate arranging a support frame flush against these features which may help to eliminate gaps between a facemask and corresponding pair of goggles when it is attached thereto. Again, eliminating gaps between an attached facemask and a pair of goggles may help to prevent a person's breath from being directed into the vents and thus interior of the goggles. However, it should also be understood that embodiments in which the support surface 100, the support surface 104, and/or the shelf 102 are neither smooth or continuous are also possible.

In addition to the support surfaces, the goggles 2 may also include appropriate attachment points such as cavities 106 and corresponding magnets 108 located within the cavities. As depicted in the figure, the goggles 2 may include the cavities 106 and the magnets 108 at various points along a bottom surface 20 of the goggles 2. More specifically, and as illustrated in the figures, the goggles 2 may include a single attachment point on either side of the nose bridge 8 corresponding to each of the legs of the support frame and two attachment points within the nose bridge 8 itself. Without wishing to be bound by theory, providing attachments at multiple points along the bottom surface 20 the goggles may help to maintain the support frame flush against the goggles and prevent gaps being formed between the facemask and goggles. While a specific number of attachment points has been depicted in the figures, and described above, greater and fewer numbers of attachment points located at different positions on the goggle exterior are also possible as the disclosure is not limited to any particular attachment arrangement between the support frame and the goggles.

FIGS. 8-11 depict one embodiment of a support frame 18. In the depicted embodiment, the support frame 18 includes a nose bridge 200 and legs 202 extending in opposite directions away from opposing sides of the nose bridge 200. As depicted in the figure, the nose bridge 200 may be triangular in shape and the legs 202 may be shaped such that they extend rearward from the nose bridge 200 and generally follow a contour of a person's face. The nose bridge 200 and legs 202 may also be shaped and arranged to complement a shape of the corresponding support surfaces located on the goggles as described above. Additionally, and as described in more detail below, since the support surfaces are arranged to avoid obscuring the vents, the support frame may be attached to the goggles without substantially obscuring the vents as well. It should be understood that other shapes of the nose bridge and legs are also possible. In addition to the nose bridge and legs, the support frame 18 may also include cavities 204 and magnets 206 disposed therein to attach the support frame to the corresponding attachment points located on the goggles as noted above.

In some embodiments it may be beneficial to provide the support frame with a lower stiffness than the goggles it is attached to. This may help to permit the support frame to more closely follow a contour of a mating surface on the goggles that it is associated with. The support frame may be provided with more flexibility than the goggles in any number of ways including, but not limited to, smaller dimensions, materials selection, cut outs, reliefs, and/or living joints to name a few.

Figure 12:
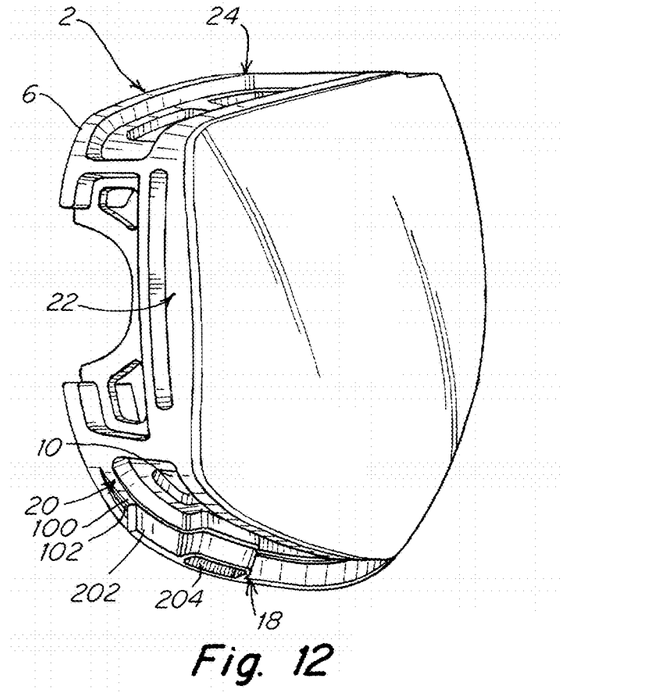
FIG. 12 is a schematic side view of a support frame coupled to a pair of goggles.
Figure 13:
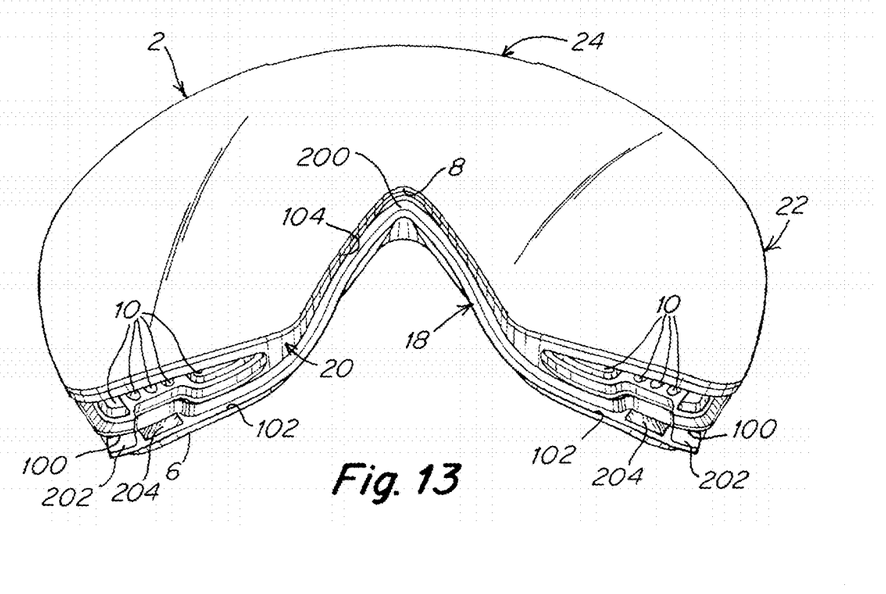
FIG. 13 is a schematic perspective bottom view of the support frame coupled to the pair of goggles depicted in FIG. 12.

Having described various embodiments of a support frame 18 and a pair of goggles 2 individually, FIGS. 12-13 illustrate a support frame 18 and a pair of goggles 2 attached to one another. As previously noted, a pair of legs 202 of the support frame 18 may be shaped and arranged such that they follow a contour of a bottom surface of the goggles and/or held flush against one or more support surfaces 100 and/or shelves 102 when they are attached to the goggles. Similarly, a nose bridge portion 200 of the support frame 18 may be shaped and arranged such that it follows a contour of the bottom surface of the goggles and/or held flush against the support surface 104 located on a nose bridge 8 of the goggles. Therefore, since both the nose bridge 200 and the legs 202 extending therefrom follow a contour of the bottom surface of the goggles and/or are held flush against corresponding portions of the goggles, the support frame 18 may follow a contour of the bottom surface of the goggles and/or be held substantially flush against the support surfaces and/or shelves of the goggles for substantially its entire length. Holding the various portions of the support frame 18 flush against the goggles 2 may help to avoid the formation of gaps between the support frame 18 and the goggles 2. In addition to the above, the figures also illustrate how the legs 200 and nose bridge 202 of the support frame may be arranged between a rearward facing surface of the goggles and the bottom vents 10 such that they do not obstruct airflow through the bottom vents 10 when the support frame is attached to the goggles. FIGS. 12-13 also illustrate how the support frame 18 extends across substantially an entire length of the bottom surface 20 of the goggles 2. However embodiments in which the support frame 18 only extends over a portion of the bottom surface 20 of the goggles 2 are also possible.

Without wishing to be bound by theory, the arrangements of the support frame 18 relative to the surfaces and the vents of the goggles 2 as described above and in the figures may offer several benefits. For example, reducing or eliminating gaps between the facemask or support frame with the goggles may help to avoid a person's exhalations from being inadvertently directed into the vents of the goggles when the facemask is attached. This arrangement may also eliminate or at least reduce the presence of gaps located between the goggles and a user's face which may reduce the amount of unintended cold air being admitted into the goggle interior.

Additionally, since the facemask and support frame do not substantially obstruct the vents of the goggles, appropriate ventilation of the goggle interior may be maintained. All the above benefits may lead to both more comfortable wear and reduced formation of condensation on the goggle lenses during use.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

The invention claimed is:

1. A goggle system comprising:
a facemask including an upper facemask portion, wherein the upper facemask portion includes all portions of the facemask positioned adjacent a set of goggles; and
a support frame operatively associated with the facemask including an upper support frame portion, wherein the upper support frame portion includes all portions of the support frame positioned adjacent the goggles, the support frame further including a nose bridge and two legs extending from the nose bridge,
wherein the nose bridge and the two legs are adapted and arranged to releasably attach the facemask to and position the facemask directly against a bottom surface of the goggles, the bottom surface facing downwardly when the goggles are worn by a user, and
wherein the nose bridge and the two legs are arranged such that when the goggles and the facemask are worn by the user the upper support frame portion and the upper facemask portion are positioned completely inward of at least one vent formed on the bottom surface of the goggles relative to a face of the user, and wherein the at least one vent is substantially unobstructed by the support frame and the facemask when the support frame is attached to the bottom surface of the goggles.

2. The goggle system of claim 1, wherein the support frame follows a contour of the bottom surface of the goggles when the support frame is attached to the bottom surface of the goggles.

3. The goggle system of claim 1, wherein the nose bridge is triangular in shape and the two legs extend away from opposing sides of the nose bridge.

4. The goggle system of claim 1, further in combination with the goggles.

5. The goggle system of claim 1, wherein the nose bridge and the two legs are disposed on one or more support surfaces of the bottom surface that do not obstruct the at least one vent when the support frame is attached to the bottom surface of the goggles.

6. The goggle system of claim 4, wherein the support frame is more flexible than the goggles.

7. The goggle system of claim 1, wherein the facemask includes an upper edge, and wherein at least a portion of the upper edge is attached to the support frame.

8. The goggle system of claim 1, wherein the support frame attaches the facemask along an entire length of the bottom surface of the goggles.

9. The goggle system of claim 1, wherein the support frame is flush against the goggles along substantially an entire length of the support frame when the support frame is attached to the goggles.

10. The goggle system of claim 1, wherein the support frame is attachable to the goggles using at least one selected from the group of a magnetic attachment, a mechanical interference fit, interlocking features, and a hook and loop fastener.

11. The goggle system of claim 1, wherein the support frame is attachable to the goggles using at least one magnetic attachment.

12. The goggle system of claim 1, wherein at least a portion of the support frame is constructed and arranged to be received in a recess in the bottom surface of the goggles.

13. The goggle system of claim 1, wherein at least a portion of a rearward facing surface of the support frame is positioned adjacent to a front facing shelf on the bottom surface of the goggles when the support frame is attached to the goggles.

14. The goggle system of claim 1, wherein the support frame includes at least one attachment point on each of the nose bridge and the two legs for attaching the support frame to the goggles.

15. The goggle system of claim 1, wherein at least a portion of the facemask is positioned between the support frame and the goggles when the support frame is attached to the goggles.

16. A goggle system comprising:
   a set of goggles including a top surface, a bottom surface, and two opposing side surfaces, wherein the bottom surface includes at least one vent;
   a facemask including an upper facemask portion, wherein the upper facemask portion includes all portions of the facemask positioned adjacent the goggles;
   a support frame operatively associated with the facemask including an upper support frame portion, wherein the upper support frame portion includes all portions of the support frame positioned adjacent the goggles, the support frame further including a nose bridge and two legs extending from the nose bridge, the bottom surface facing downwardly when the goggles are worn by a user;
   wherein the nose bridge and the two legs are releasably attachable to the bottom surface of the goggles to attach the facemask associated with the support frame to the bottom surface of the goggles and position the facemask directly against the bottom surface of the goggles; and
   wherein the nose bridge and the two legs are arranged such that when the goggles are worn by the user the upper support frame portion and the upper facemask portion are positioned completely inward of the at least one vent formed on the bottom surface of the goggles relative to a face of the user, and wherein the at least one vent formed on the bottom surface of the goggles is substantially unobstructed by the support frame and the facemask when the support frame is attached to the bottom surface of the goggles.

17. The goggle system of claim 16, wherein the support frame follows a contour of the bottom surface of the goggles when the support frame is attached to the bottom surface of the goggles.

18. The goggle system of claim 16, wherein the nose bridge is triangular in shape and the two legs extend away from opposing sides of the nose bridge.

19. The goggle system of claim 16, wherein the support frame is more flexible than the goggles.

20. The goggle system of claim 16, wherein the nose bridge and the two legs are disposed on one or more support surfaces of the bottom surface that do not obstruct the at least one vent when the support frame is attached to the bottom surface of the goggles.

21. The goggle system of claim 16, wherein at least a portion of the facemask is positioned between the support frame and the goggles when the support frame is attached to the goggles.

22. The goggle system of claim 16, wherein the facemask includes an upper edge, and wherein at least a portion of the upper edge is attached to the support frame.

23. The goggle system of claim 16, wherein the support frame attaches the facemask along an entire length of the bottom surface of the goggles.

24. The goggle system of claim 16, wherein the support frame is flush against the goggles along substantially an entire length of the support frame when the support frame is attached to the goggles.

25. The goggle system of claim 16, wherein the support frame is attachable to the goggles using at least one selected from the group of a magnetic attachment, a mechanical interference fit, interlocking features, and a hook and loop fastener.

26. The goggle system of claim 16, wherein the support frame is attachable to the goggles using at least one magnetic attachment.

27. The goggle system of claim 16, wherein at least a portion of the support frame is received in a recess in the bottom surface of the goggles.

28. The goggle system of claim 16, wherein at least a portion of a rearward facing surface of the support frame is positioned adjacent to a front facing shelf on the bottom surface of the goggles when the support frame is attached to the goggles.

29. The goggle system of claim 16, wherein the support frame includes at least one attachment point on each of the nose bridge and the two legs for attaching the support frame to the goggles.

* * * * *